United States Patent
Fey

(10) Patent No.: US 9,354,213 B2
(45) Date of Patent: May 31, 2016

(54) METHOD AND DEVICE FOR CORRECTING A CHARACTERISTIC CURVE OF A TWO-STEP LAMBDA OXYGEN SENSOR

(71) Applicant: Michael Fey, Wiernsheim (DE)

(72) Inventor: Michael Fey, Wiernsheim (DE)

(73) Assignee: Robert Bosch GmbH, Stuttgart (DE)

( * ) Notice: Subject to any disclaimer, the term of this patent is extended or adjusted under 35 U.S.C. 154(b) by 356 days.

(21) Appl. No.: 13/933,920

(22) Filed: Jul. 2, 2013

(65) Prior Publication Data

US 2014/0007644 A1      Jan. 9, 2014

(30) Foreign Application Priority Data

Jul. 5, 2012    (DE) .......................... 10 2012 211 683

(51) Int. Cl.
| | | |
|---|---|---|
| *G01M 15/04* | (2006.01) | |
| *G01N 33/00* | (2006.01) | |
| *F02D 41/14* | (2006.01) | |
| *G01M 15/10* | (2006.01) | |
| G01N 27/417 | (2006.01) | |
| F02D 41/24 | (2006.01) | |

(52) U.S. Cl.
CPC ........ *G01N 33/0006* (2013.01); *F02D 41/1454* (2013.01); *F02D 41/1458* (2013.01); *G01M 15/104* (2013.01); *F02D 41/2474* (2013.01); *G01N 27/4175* (2013.01)

(58) Field of Classification Search
CPC ............ G01M 15/104; G01N 33/0006; F02D 41/1458; F02D 41/1493; Y02T 10/47
See application file for complete search history.

(56) References Cited

U.S. PATENT DOCUMENTS

| | | | | |
|---|---|---|---|---|
| 3,973,529 A | * | 8/1976 | Wessel ................. | F02D 41/182 123/676 |
| 4,244,339 A | * | 1/1981 | Gorille ..................... | F02P 5/15 123/406.44 |
| 4,463,594 A | * | 8/1984 | Raff .................... | F02D 41/1481 123/694 |
| 4,720,335 A | * | 1/1988 | Fukushima ........ | G01N 27/4075 204/291 |

(Continued)

FOREIGN PATENT DOCUMENTS

| | | |
|---|---|---|
| DE | 38 27 978 | 5/1989 |
| DE | 198 60 463 | 7/2000 |
| DE | 10 2010 027 984 | 10/2011 |

*Primary Examiner* — Peter Macchiarolo
*Assistant Examiner* — Nathaniel Kolb
(74) *Attorney, Agent, or Firm* — Norton Rose Fulbright US LLP

(57) ABSTRACT

A method and device for correcting a voltage-lambda characteristic curve of a two-step lambda oxygen sensor in an exhaust tract relative to a reference-voltage lambda characteristic curve of the oxygen sensor; a deviation in the characteristic curve relative to the reference characteristic curve at lambda=1 being corrected; based on a value pair on the reference-voltage lambda characteristic curve, the composition of the air-fuel mixture supplied to the engine being changed toward lambda=1; the actual value of lambda being inferred from the change in the composition of the air-fuel mixture. The adaptation of the operating parameters of the oxygen sensor is intended to eliminate the cause of a deviation. Efforts are not merely directed to adapting the deviation to the reference characteristic curve by shifting the voltage-lambda characteristic curve. Effects, which may lead to tolerance- or aging-induced falsifications of the voltage-lambda characteristic curve, can be fully compensated.

18 Claims, 1 Drawing Sheet

(56) References Cited

U.S. PATENT DOCUMENTS

| | | | | |
|---|---|---|---|---|
| 5,249,453 A | * | 10/1993 | Usami | G01N 27/4065 204/408 |
| 5,553,593 A | * | 9/1996 | Schnaibel | F02D 41/047 123/682 |
| 2004/0016228 A1 | * | 1/2004 | Yasui | G01N 27/4067 60/285 |
| 2009/0138182 A1 | * | 5/2009 | Bruhn | F02D 41/1476 701/109 |
| 2014/0012486 A1 | * | 1/2014 | Fey | F02D 41/00 701/103 |

* cited by examiner

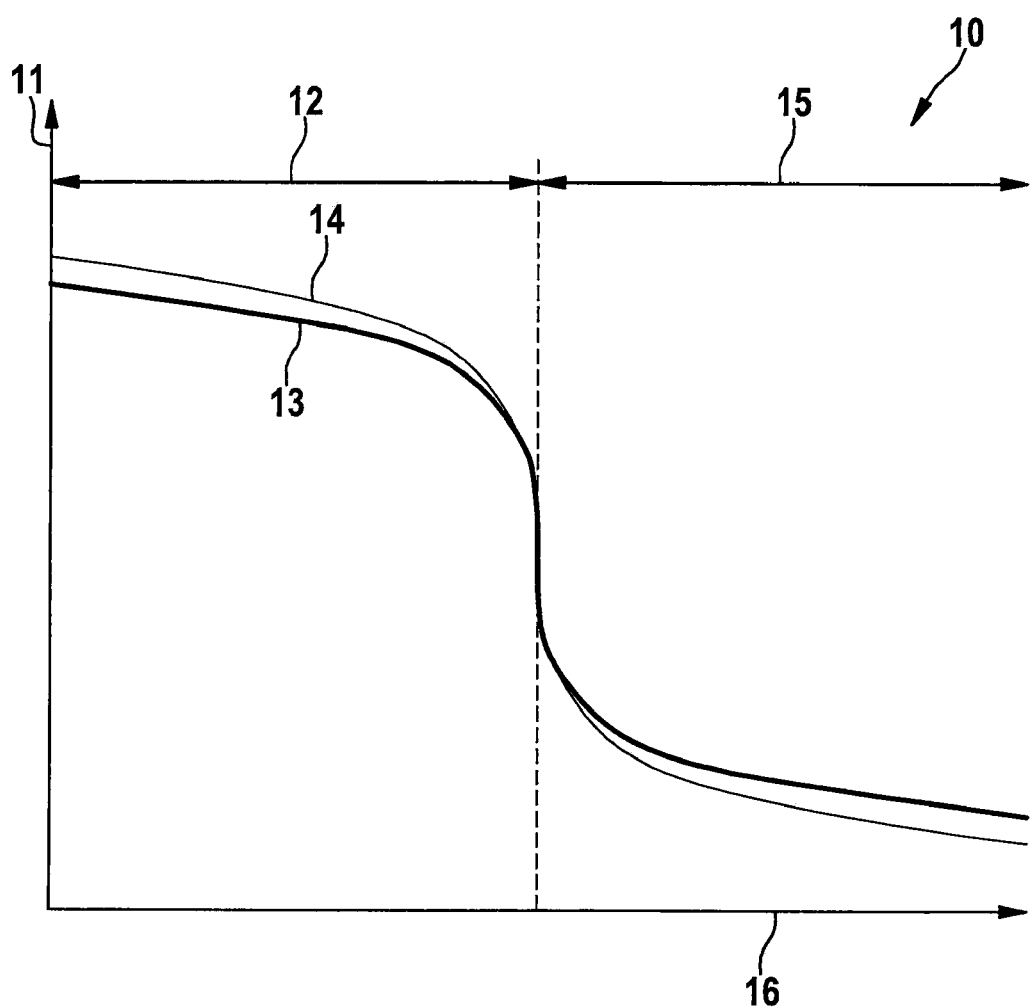

METHOD AND DEVICE FOR CORRECTING A CHARACTERISTIC CURVE OF A TWO-STEP LAMBDA OXYGEN SENSOR

RELATED APPLICATION INFORMATION

The present application claims priority to and the benefit of German patent application no. 10 2012 211 683.4, which was filed in Germany on Jul. 5, 2012, the disclosure of which is incorporated herein by reference.

FIELD OF THE INVENTION

The present invention relates to a method for correcting a voltage-lambda characteristic curve of a two-step lambda oxygen sensor disposed in an exhaust tract of an internal combustion engine relative to a reference-voltage lambda characteristic curve of the two-step lambda oxygen sensor. The present invention also relates to a device for correcting a voltage-lambda characteristic curve of a two-step lambda oxygen sensor disposed in an exhaust tract relative to a reference-voltage lambda characteristic curve of the two-step lambda oxygen sensor.

BACKGROUND INFORMATION

Lambda oxygen sensors are used in the exhaust system of internal combustion engines to optimize pollutant emissions and the exhaust-gas aftertreatment. The lambda oxygen sensors determine the oxygen content of the exhaust gas which is then used for the closed-loop control of the air-fuel mixture supplied to the internal combustion engine and thus the exhaust-gas lambda number upstream of a catalytic converter. A lambda control loop controls the supplying of air and fuel to the internal combustion engine in closed loop to achieve an exhaust gas composition that is optimal for the exhaust-gas aftertreatment by the catalytic converters provided in the exhaust tract of the internal combustion engine. In the case of spark ignition engines, a lambda of 1, thus a stoichiometric ratio of air to fuel is typically controlled in closed loop. The pollutant emissions of the internal combustion engine can thus be minimized.

Various forms of lambda oxygen sensors are in use. In the case of a two-step lambda oxygen sensor, also referred to as a discrete-level sensor or Nernst sensor, the voltage-lambda characteristic curve exhibits a step change in the characteristic curve profile at lambda=1. Therefore, it essentially allows a distinction to be made between rich exhaust gas ($\lambda<1$) during internal combustion engine operation characterized by excess fuel and lean exhaust gas ($\lambda>1$) during operation characterized by excess air, and permits a closed-loop control of the exhaust gas to a lambda of 1.

Using a broadband lambda oxygen sensor, also referred to as a continuous or linear lambda oxygen sensor, the lambda value in the exhaust gas can be measured within a broad range around lambda=1. Thus, for example, an internal combustion engine can also be controlled in closed loop toward a lean operation characterized by excess air.

By linearizing the sensor characteristic, a continuous closed-loop lambda control upstream of the catalytic converter is possible within a limited lambda range even when a less expensive, two-step lambda oxygen sensor is used. This requires that there be a unique relationship between the sensor voltage of the two-step lambda oxygen sensor and lambda. This relationship must exist for the entire service life of the two-step lambda oxygen sensor since, otherwise, the accuracy of the closed-loop control will not suffice, and unacceptably high emissions can occur. This requirement is not met due to manufacturing tolerances and the aging effects of the two-step lambda oxygen sensor. For that reason, two-step lambda oxygen sensors upstream of the catalytic converter are mostly used in the context of a two-step closed-loop control. This has the disadvantage that, in operating modes, for which a lean or rich air-fuel mixture is required, for example, for catalytic converter diagnostics or for component protection, the target lambda can only be precontrolled, but not controlled in closed loop.

It is believed to be understood that there are various methods for calibrating the voltage-lambda characteristic curve of two-step lambda oxygen sensors to ensure that they can be used for a continuous control over the entire operational life thereof.

German Patent Application DE 3827978 discusses determining and compensating for a voltage offset, which is constant over the entire lambda range, of the voltage-lambda characteristic curve in question using a reference-voltage lambda characteristic curve of the two-step lambda oxygen sensor as a basis for comparison by adjusting the sensor voltage upon trailing throttle fuel cutoff of the internal combustion engine. Furthermore, German Patent Application DE 102010027984 A1 describes a method for operating an exhaust system of an internal combustion engine where at least one parameter of the exhaust gas flowing in an exhaust tract is measured by an exhaust-gas sensor. In accordance therewith, fresh air is supplied to the exhaust tract upstream of the exhaust-gas sensor via a fresh air supply assigned to the exhaust system during one operating state of the internal combustion engine in which injection and fuel combustion do not take place, and the exhaust-gas sensor is adjusted during this time and/or subsequently thereto.

However, the voltage offset can only be adequately compensated when it is equally pronounced, not only in the case of trailing throttle fuel cutoff given corresponding oxygen-containing exhaust gas, but also over the entire lambda range. This can be the case when the voltage offset is due to a single cause. For the most part, however, there are several overlapping reasons why the voltage-lambda characteristic curve deviates from a reference-voltage lambda characteristic curve. These may be more or less salient in different lambda ranges, whereby the voltage offset changes as a function of the exhaust gas lambda. In particular, the causes in the lean and rich lambda ranges can vary in saliency. In the case of trailing throttle fuel cutoff, such a lambda-dependent voltage offset cannot be adequately compensated by an adjustment. A further drawback of the method resides in that present-day engine designs feature fewer and fewer trailing-throttle phases, thereby limiting the possibility of such trailing-throttle adjustments.

German publication DE3837984 discusses a method for compensating for a shift of the lambda-1 step of the voltage-lambda characteristic curve by a setpoint control that includes a second lambda oxygen sensor disposed downstream.

German publication DE19860463 discusses a method for determining the composition of the fuel-air mixture of a combustion engine during operation at a given setpoint value deviation from lambda=1, where the actual value deviation from lambda=1 is determined by temporarily adjusting the composition and evaluating the resulting reaction of a lambda oxygen sensor. It provides for a step-type adjustment by a defined value toward lambda=1 to be initially made, and for the lambda value to be subsequently further modified at a defined rate of change until the lambda oxygen sensor reacts, and for the actual deviation to be determined from the value of the step-type adjustment, the rate of change, and the time until the reaction of the lambda oxygen sensor is ascertained.

Using the method, an offset of the voltage-lambda characteristic curve of a two-step lambda oxygen sensor can be recognized. It is disadvantageous that differences in various lambda ranges remain unconsidered in determining the actual value deviation from lambda=1. This can falsify the result to such an extent that the accuracy required for a continuous closed-loop lambda control using a two-step lambda oxygen sensor disposed upstream of the catalytic converter in order to recognize a characteristic curve offset, is not met.

SUMMARY OF THE INVENTION

It is, therefore, an object of the present invention to provide a reliable method for reducing a voltage offset of a two-step lambda oxygen sensor to render possible a continuous closed-loop lambda control using the two-step lambda oxygen sensor.

It is also an object of the present invention to provide a device for carrying out the method.

The present invention relates to a method for correcting a voltage-lambda characteristic curve of a two-step lambda oxygen sensor disposed in an exhaust tract of an internal combustion engine relative to a reference-voltage lambda characteristic curve of the two-step lambda oxygen sensor; a deviation in the characteristic curve relative to the reference-voltage lambda characteristic curve at lambda=1 being corrected; on the basis of a value pair on the reference-voltage lambda characteristic curve, the composition of the air-fuel mixture supplied to the internal combustion engine being changed toward lambda=1; and the actual value of lambda being inferred from the change in the composition of the air-fuel mixture.

The present invention also relates to a device for correcting a voltage-lambda characteristic curve of a two-step lambda oxygen sensor disposed in an exhaust tract relative to a reference-voltage lambda characteristic curve of the two-step lambda oxygen sensor; a deviation in the characteristic curve relative to the reference-voltage lambda characteristic curve at lambda=1 being corrected; a control device being provided, which, on the basis of a value pair on the reference-voltage lambda characteristic curve, changes the composition of the air-fuel mixture supplied to the internal combustion engine toward lambda=1, and, from the change in the composition of the air-fuel mixture, derives the actual value of lambda, and the control device being provided for adjusting the operating parameters of the two-step lambda oxygen sensor.

In terms of the method, the object of the present invention is achieved in that operating parameters of the two-step lambda oxygen sensor are adjusted in consideration of the deviation between the lambda value from the value pair and the actual value of lambda in a way that allows a deviation between the voltage-lambda characteristic curve of the two-step lambda oxygen sensor and the reference-voltage lambda characteristic curve to be corrected. In this case, the reference-voltage lambda characteristic curve indicates the relationship between the output voltage of the two-step lambda oxygen sensor and the lambda value, given an intact two-step lambda oxygen sensor, in the context of standardized operating parameters, without allowing for manufacturing tolerances.

The inventive adaptation of the operating parameters of the two-step lambda oxygen sensor advantageously eliminates the cause of a deviation. Efforts are not merely directed to adjusting the deviation by shifting the voltage-lambda characteristic curve in the direction of the reference characteristic curve. Effects, which may lead to tolerance- or aging-induced falsifications of the voltage-lambda characteristic curve, can be fully compensated. An additive or multiplicative effect of a falsification is correctly considered. Falsifications that are pronounced to varying degrees in the profile of the sensor's characteristic curve, in particular differences in the lean and the rich lambda range, are correctly considered.

As already described, in determining the actual lambda value, the value lambda=1 may be approached starting from a value pair, and the actual lambda value may be determined from the adjustment. Alternatively, using lambda=1 as a basis, the value pair may also be approached, and the actual lambda value may be determined from the adjustment.

The method manages without additional trailing-throttle fuel cutoff phases and is thus also suited for engine designs not having any or having few trailing-throttle phases. The method makes it possible for a low-cost, two-step lambda oxygen sensor to be used for an accurate, continuous lambda control upstream of the catalytic converter.

An especially precise determination of the actual value of lambda is achieved in that, on the basis of the value pair on the reference-voltage lambda characteristic curve, a change in the composition of the air-fuel mixture beyond lambda=1 is implemented in that the composition of the air-fuel mixture is changed in a ramp shape at least within the range around lambda=1, and in that the actual lambda in the value pair is determined from the change in the composition of the air-fuel mixture until the output voltage of the two-step lambda oxygen sensor corresponding to lambda=1 is reached. In this case, the ramp-shaped curve may begin already with the value pair. In a faster variant of the method, a step-type lambda change may be carried out until lambda=1 is closely approached, and lambda=1 may then be crossed in a ramp-shaped fashion.

In a further refinement of the method, at least one operating parameter causing the deviation is inferred from the deviation between the profiles of the voltage-lambda characteristic curve and the reference-voltage lambda characteristic curve of the two-step lambda oxygen sensor. The operating parameter causing the deviation is selectively adapted in subsequent processes.

If a preceding adaptation of the voltage-lambda characteristic curve is adjusted upon setting of the operating parameters, it is possible to further improve the correction of the voltage-lambda characteristic curve. For example, if a constant offset of the voltage-lambda characteristic curve had been adapted during a trailing throttle fuel cutoff, but the temperature had been recognized as the operating parameter to be corrected, the constant correction must be canceled in the lean branch of the sensor's characteristic curve. The correction in the lean branch is completely achieved by adapting the temperature of the two-step lambda oxygen sensor.

In one embodiment of the method, the correction of the voltage-lambda characteristic curve is undertaken in an iterative process that includes the steps of determining the actual value of lambda and the deviation thereof from the reference-voltage lambda characteristic curve; adjusting the operating parameter of the two-step lambda oxygen sensor in consideration of the deviation; adjusting a previous adaptation of the voltage-lambda characteristic curve. The differences between the voltage-lambda characteristic curve and the reference-voltage lambda characteristic curve may be hereby corrected in a particularly effective manner.

If the correction of the voltage offset is checked for plausibility by taking repeated measurements and/or by taking repeated measurements and averaging or filtering for the same value pair, or by taking measurements for various value pairs, it is possible to minimize the effect of signal interference and tolerances in the measured value acquisition.

Aging effects or tolerance-related deviations occur only very slowly. Therefore, prior to a renewed adjustment of the operating parameters of the two-step lambda oxygen sensor, it is advantageous to use the values of the operating parameters set in a previous operating cycle of the internal combustion engine, and/or to draw upon the values of the operating parameters set in a previous operating cycle of the internal combustion engine in order to check for plausability. In this manner, an effectively corrected voltage-lambda characteristic curve is already available at the beginning of an operating cycle.

If there is still no correction of operating parameters of the two-step lambda oxygen sensor from a previous driving test cycle, it is advantageous when the value pair to be checked is selectively adjusted. If a correction already exists from a previous driving test cycle, a plausibility check may follow in that the voltage offset is corrected in the case of a value pair occurring during operation of the internal combustion engine. In such a case, there is no need for an active intervention in the operation of the internal combustion engine.

The temperature of the two-step lambda oxygen sensor influences the voltage-lambda characteristic curve. It is, therefore, advantageous when the temperature of the two-step lambda oxygen sensor is adapted as a function of the power fed to the heating of the two-step lambda oxygen sensor.

A correction of the voltage-lambda characteristic curve is able to be determined by adapting the temperature of the two-step lambda oxygen sensor in that, from a ratio of first shift of the voltage-lambda characteristic curve relative to the reference-voltage lambda characteristic curve within the range of lambda <1 to a second shift of the voltage-lambda characteristic curve relative to the reference-voltage lambda characteristic curve within the range of lambda >1, the temperature of the two-step lambda oxygen sensor is inferred as the operating parameter to be adapted. Typically, a temperature change in the two-step lambda oxygen sensor is expressed as a signal change in the rich branch that is six times as great as in the lean branch. When the correction is made, it may be considered that an offset is already completely compensated in the lean branch by a previously undertaken compensation of a constant offset of the sensor's characteristic curve, while an offset in the rich branch is typically only compensated by ⅙. Therefore, this previously undertaken compensation may initially be advantageously canceled for a correction by adapting the temperature.

In terms of the device, the object of the present invention is achieved in that, in the control device, a program execution or a circuit is provided for adjusting the operating parameters of the two-step lambda oxygen sensor in consideration of the deviation between the lambda value from the value pair and the actual value of lambda in such a way that a deviation between the voltage-lambda characteristic curve of the two-step lambda oxygen sensor and the reference-voltage lambda characteristic curve is corrected. The thus undertaken correction has the advantage that tolerance- or aging-related causes of deviations are eliminated, and there is no need for a precise knowledge of additive or multiplicative components of deviations.

The present invention is clarified in greater detail in the following on the basis of an exemplary embodiment illustrated in the figure.

BRIEF DESCRIPTION OF THE DRAWING

FIG. 1 shows a voltage-lambda diagram 10 of a two-step lambda oxygen sensor in that an output voltage of the two-step lambda oxygen sensor is plotted along a voltage axis 11 and a lambda axis 16.

DETAILED DESCRIPTION

For a brand-new, two-step lambda oxygen sensor under standard conditions, a reference-voltage lambda characteristic curve 13 applies. When reference-voltage lambda characteristic curve 13 is observed, a continuous control of an air-fuel mixture supplied to an internal combustion engine may also follow using a low-cost, two-step lambda oxygen sensor in an exhaust tract mounted upstream of a catalytic converter within a certain lambda range. There is also a unique relationship between the output voltage of the two-step lambda oxygen sensor, both in a rich region 12 where lambda <1, as well as in a lean region 15 where lambda >1.

Tolerances and aging cause deviations that do not permit a long-term, continuous use of the two-step lambda oxygen sensor for this purpose. For example, if manufacturing tolerances, aging, as well as an increase in the temperature of the two-step lambda oxygen sensor induce a change in the characteristic curve, a voltage-lambda characteristic curve 14 is derived. This is not transferable to reference-voltage lambda characteristic 13 by adaptation of a constant offset. In such a case, the manufacturing tolerance effects a decrease both in lean region 15 as well as in rich region 12. In addition, the increase in temperature effects a reduction in rich region 12. If a correction is merely undertaken by a characteristic curve shift along voltage axis 11, then it is only possible to correct a portion of the temperature-induced deviation. In lean region 15, a complete correction is possible; in rich region 12, typically only ⅙ of the characteristic curve falsification. Using the method according to the present invention, the temperature of the two-step lambda oxygen sensor is adapted in a way that allows voltage-lambda characteristic curve 14 to be corrected over entire rich region 12 and lean region 15 toward reference-voltage lambda characteristic curve 13.

What is claimed is:

1. A method for correcting a voltage-lambda characteristic curve of a two-step lambda oxygen sensor disposed in an exhaust tract of an internal combustion engine relative to a reference voltage-lambda characteristic curve of the two-step lambda oxygen sensor, the method comprising:
   determining an actual value of the voltage-lambda and a deviation thereof from the reference voltage-lambda characteristic curve;
   changing, based on a value pair on the reference voltage-lambda characteristic curve, the composition of the air-fuel mixture supplied to the internal combustion engine towards lambda=1;
   inferring the actual value of lambda from the change in the composition of the air-fuel mixture; and
   adjusting, in consideration of the deviation between the lambda value from the value pair and the actual value of lambda, the operating parameters of the two-step lambda oxygen sensor so as to correct a deviation between the voltage-lambda characteristic curve of the two-step lambda oxygen sensor and the reference voltage-lambda characteristic curve at lambda=1, and
   wherein the correction of the voltage-lambda characteristic curve is determined by adapting a temperature of the two-step lambda oxygen sensor, the temperature being inferred as the operating parameter to be adapted from a ratio of a first shift of the voltage-lambda characteristic curve relative to the reference voltage-lambda characteristic curve within the range of lambda <1 to a second shift of the voltage-lambda characteristic curve relative to the reference voltage-lambda characteristic curve within the range of lambda >1.

2. The method of claim 1, wherein, based on the value pair on the reference voltage-lambda characteristic curve, a change in the composition of the air-fuel mixture beyond lambda =1 is implemented in that the composition of the air-fuel mixture is changed in a ramp shape at least within the range around lambda =1, and wherein the actual lambda in the value pair is determined from the change in the composition of the air-fuel mixture until the output voltage of the two-step lambda oxygen sensor corresponding to lambda =1 is reached.

3. The method of claim 1, wherein at least one operating parameter causing the deviation is inferred from the deviation between the profiles of the voltage-lambda characteristic curve and the reference voltage-lambda characteristic curve of the two-step lambda oxygen sensor.

4. The method of claim 1, wherein a preceding adaptation of the voltage-lambda characteristic curve is adjusted when the operating parameters are set.

5. The method of claim 1, wherein the correction of the voltage-lambda characteristic curve is undertaken in an iterative process including
an adjusting of a previous adaptation of the voltage-lambda characteristic curve.

6. The method of claim 1, wherein the correction of the voltage offset is checked for plausibility by taking repeated measurements or by taking repeated measurements and by averaging or filtering for the same value pair, or by taking measurements for various value pairs.

7. The method of claim 1, wherein, prior to a renewed adjustment of the operating parameters, the values of the operating parameters set in a previous operating cycle of the internal combustion engine are used, and/or the values of the operating parameters set in a previous operating cycle of the internal combustion engine are retrieved in order to check for plausibility.

8. The method of claim 1, wherein the value pair to be checked is selectively adjusted, and/or the voltage offset is corrected in the case of a value pair occurring during operation of the internal combustion engine.

9. The method of claim 1, wherein the temperature of the two-step lambda oxygen sensor is adapted as the operating parameter.

10. A device for correcting a voltage-lambda characteristic curve of a two-step lambda oxygen sensor disposed in an exhaust tract of an internal combustion engine relative to a reference voltage-lambda characteristic curve of the two-step lambda oxygen sensor, comprising:
a control device to determine an actual value of the voltage-lambda and a deviation thereof from the reference voltage-lambda characteristic curve, and to implement, based on a value pair on the reference voltage-lambda characteristic curve, a change in the composition of the air-fuel mixture supplied to the internal combustion engine toward lambda =1, and to derive, from the change in the composition of the air-fuel mixture, the actual value of lambda;
wherein the control device is configured to adjust the operating parameters of the two-step lambda oxygen sensor and to adjust the operating parameters of the two-point lambda probe in consideration of the deviation between the lambda value from the value pair and the actual value of lambda so as to correct a deviation between the voltage-lambda characteristic curve of the two-step lambda oxygen sensor and the reference voltage-lambda characteristic curve at lambda =1, and
wherein the correction of the voltage-lambda characteristic curve is determined by adapting a temperature of the two-step lambda oxygen sensor, the temperature being inferred as the operating parameter to be adapted from a ratio of a first shift of the voltage-lambda characteristic curve relative to the reference voltage-lambda characteristic curve within the range of lambda <1 to a second shift of the voltage-lambda characteristic curve relative to the reference voltage-lambda characteristic curve within the range of lambda >1.

11. The device of claim 10, wherein, based on the value pair on the reference voltage-lambda characteristic curve, a change in the composition of the air-fuel mixture beyond lambda =1 is implemented in that the composition of the air-fuel mixture is changed in a ramp shape at least within the range around lambda =1, and wherein the actual lambda in the value pair is determined from the change in the composition of the air-fuel mixture until the output voltage of the two-step lambda oxygen sensor corresponding to lambda =1 is reached.

12. The device of claim 10, wherein at least one operating parameter causing the deviation is inferred from the deviation between the profiles of the voltage-lambda characteristic curve and the reference voltage-lambda characteristic curve of the two-step lambda oxygen sensor.

13. The device of claim 10, wherein a preceding adaptation of the voltage-lambda characteristic curve is adjusted when the operating parameters are set.

14. The device of claim 10, wherein the correction of the voltage-lambda characteristic curve is undertaken in an iterative process including an adjusting of a previous adaptation of the voltage-lambda characteristic curve.

15. The device of claim 10, wherein the correction of the voltage offset is checked for plausibility by taking repeated measurements or by taking repeated measurements and by averaging or filtering for the same value pair, or by taking measurements for various value pairs.

16. The device of claim 10, wherein, prior to a renewed adjustment of the operating parameters, the values of the operating parameters set in a previous operating cycle of the internal combustion engine are used, and/or the values of the operating parameters set in a previous operating cycle of the internal combustion engine are retrieved in order to check for plausibility.

17. The device of claim 10, wherein the value pair to be checked is selectively adjusted, and/or the voltage offset is corrected in the case of a value pair occurring during operation of the internal combustion engine.

18. The device of claim 10, wherein the temperature of the two-step lambda oxygen sensor is adapted as the operating parameter.

* * * * *